United States Patent [19]

Narayanan et al.

[11] Patent Number: 4,762,127

[45] Date of Patent: Aug. 9, 1988

[54] APPARATUS AND METHOD FOR ENLARGING THE ENDS OF A VESSEL PRIOR TO ANASTOMOSIS

[75] Inventors: Krishna Narayanan; Marc D. Liang, both of Pittsburgh, Pa.

[73] Assignee: The Montefiore Hospital Association of Western Pennsylvania, Pittsburgh, Pa.

[21] Appl. No.: 38,652

[22] Filed: Apr. 15, 1987

[51] Int. Cl.$^4$ .............................................. A61B 17/11
[52] U.S. Cl. .............................. 128/334 R; 128/325; 128/344
[58] Field of Search ................ 128/344, 348.1, 334 R, 128/775, 778, 325; 604/96–103

[56] References Cited

U.S. PATENT DOCUMENTS

| | | | |
|---|---|---|---|
| 1,729,296 | 9/1929 | Sarason | 128/344 |
| 3,467,101 | 9/1969 | Fogarty et al. | 128/348.1 |
| 3,480,017 | 11/1969 | Shute | 128/344 |
| 3,799,170 | 3/1974 | Walsh et al. | 128/344 |
| 3,900,033 | 8/1975 | Leininger et al. | 128/344 |
| 3,978,863 | 9/1976 | Fettel et al. | 128/348.1 |
| 4,230,119 | 10/1980 | Blum | 128/334 R |
| 4,312,353 | 1/1982 | Shahbabian | 128/344 |
| 4,446,867 | 5/1984 | LeVeen et al. | 128/344 |
| 4,448,195 | 5/1984 | LeVeen et al. | 128/344 |
| 4,653,514 | 3/1987 | Shapiro | 128/778 |

Primary Examiner—Dalton L. Truluck
Assistant Examiner—Frank Wilkens
Attorney, Agent, or Firm—Harry B. Keck

[57] ABSTRACT

An improved method for expanding the open ends of human vessels employs an expandable cell which can be inflated a bubble at the open end of a vessel. The method is carried out with a novel closed end cell which can be connected to a source of fluidized pressure such a hypodermic syringe and, in its relaxed state can be introduced into the open end of the vessel for subsequent expansion into a bubble of the desired diameter to cause uniform length extension of the open end of the vessel. The cell may be prestressed or weakened to establish the location of bubble formation within the cell.

5 Claims, 1 Drawing Sheet

U.S. Patent     Aug. 9, 1988     4,762,127
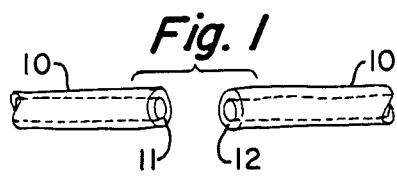
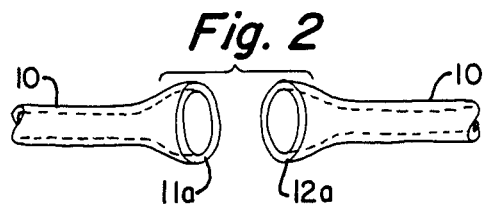
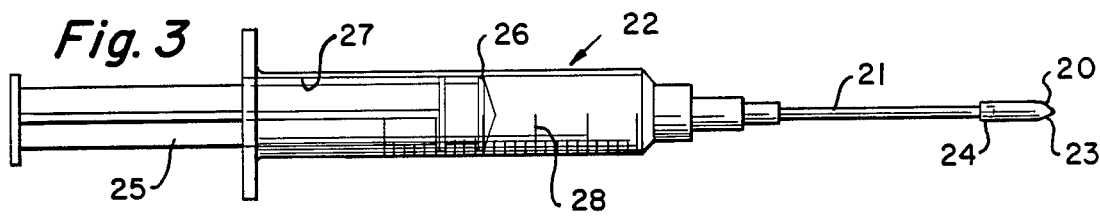
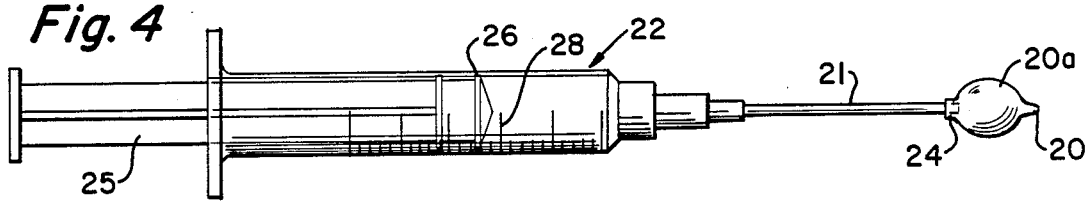
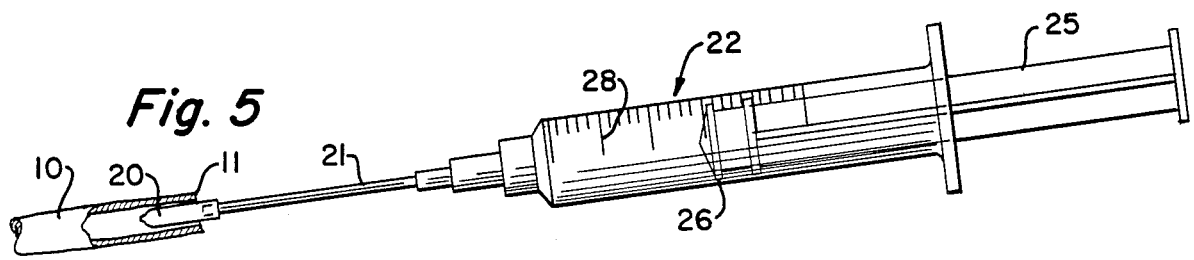
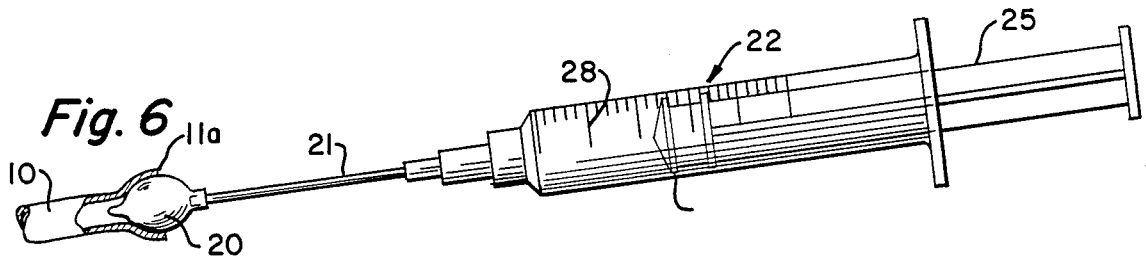
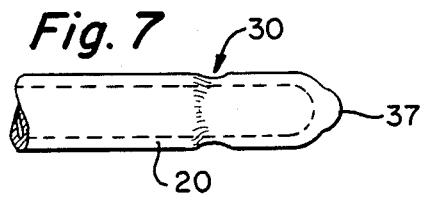
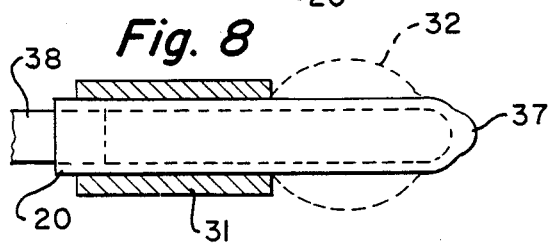
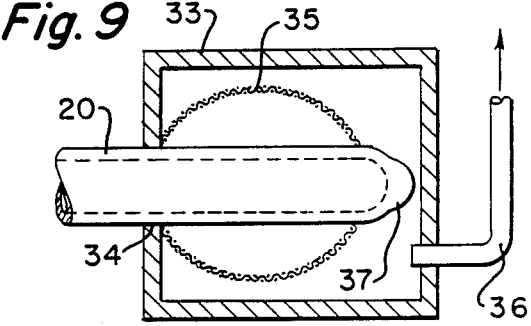

APPARATUS AND METHOD FOR ENLARGING THE ENDS OF A VESSEL PRIOR TO ANASTOMOSIS

BACKGROUND OF THE INVENTION

1. Field of the Invention

This invention concerns a method for enlarging the open ends of vessels, principally blood vessels, prior to anastomosis.

2. Description of the Prior Art

In the field of microsurgery, anastomosis of blood vessels (veins and arteries) is critical. Typically, open ends of veins to be joined require about seven peripheral stitches; open ends of arteries require about eight to nine peripheral stitches. The success of microsurgery in many respects depends upon the effectiveness of the blood vessel anastomosis. Typically blood vessel anastomosis requires about one hour per vessel and is carried out with the vessel ends retained in a clamping device. To facilitate suturing of the abutted vessel ends, the procedure of choice is for the surgeon to insert the tips of a pair of forceps into the open vessel end and allow the forceps to spring apart so that the tips of the forceps stretch the walls of the vessel adjacent to the open end. By retaining the forceps in the partially opened position, the surgeon can enlarge the open end of the vessel. The enlargement continues for a limited period of time to provide an increased length periphery for sutures. The use of forceps stretches the blood vessel across its diameter and concentrates most of the stress at diametrically opposed areas which are contacted by the open forceps. The amount of stretching depends upon the skill of the operator in a tactile sensitivity to the forceps.

STATEMENT OF THE PRESENT INVENTION

According to the present invention, anastomosis can be improved by providing an apparatus which includes a closed, resilient, expansible, tubular member comprising a membrane which is expandable into a bubble positionable at the open end of a blood vessel to provide uniform, predictable vessel expansion. The invention also contemplates the process of providing uniform stress over the inner wall of the blood vessel which is to be expanded prior to anastomosis.

According to the present invention, the vessel end is gently and uniformly stretched to a larger diameter which can be determined by controlling the final diameter of the expanding bubble. In a preferred embodiment, the bubble is connected to a hypodermic syringe. The inflated diameter of the bubble can be controlled by the operator when the syringe plunger is advanced to a predetermined calibration reading on the syringe. Alternatively the bubble may be connected to any easily controlled source of fluid pressure.

The bubble preferably is formed from expandable rubber or plastic of closed-end tubular configuration which may be prestressed to locate the bubble position. Prestressing may occur by weakening the wall thickness of the membrane, or by prestressing the membrane under controlled conditions to weaken the membrane where the expansion is desired.

DESCRIPTION OF THE DRAWINGS

FIG. 1 is a schematic illustration of two confronting open ends of a vessel to be joined by anastomosis.

FIG. 2 is a perspective illustration of two confronting vessel ends which have been enlarged in accordance with the present invention prior to anastomosis.

FIG. 3 is a view of a hypodermic syringe having an expandable cell in its relaxed state.

FIG. 4 is an illustration of the hypdermic syringe of FIG. 3 with the expandable cell in its expanded state.

FIG. 5 is a schematic illustration of the hypodermic syringe of FIG. 4 having its expandable cell inserted into the open end of a vessel.

FIG. 6 is an illustration of the hypodermic syringe of FIG. 4 with the expanded cell in its vessel-expanding state.

FIG. 7 is a perspective illustration of an expandable cell having weakened side walls to locate the region of expansion for the cell.

FIG. 8 is an expandable cell having its open end tightly enclosed in a sleeve to permit pre-expansion of the cell in a desired location.

FIG. 9 is an illustration of an expansion box for pre-expanding an expandable cell in a desired location.

DESCRIPTION OF THE PREFERRED EMBODIMENT

FIG. 1 illustrates two abutting ends of a blood vessel 10 to be joined by anastomosis. The abutted ends 11, 12 ordinarily have an outer diameter from 0.7 to 1.2 millimeters and require about seven peripheral stitches for a vein and about eight to nine peripheral stitches for an artery to achieve successful anastomosis. The blood vessel 10 has an inner wall and an outer wall.

FIG. 2 illustrates the same vessel 10 having its open ends 11a, 12a expanded to provide an extended periphery which facilitates suturing of the two open ends 11a, 12a. Heretofore expanded open ends 11a, 12a have been formed by inserting forceps into the open ends 11, 12 (FIG. 1) and allowing the forceps to spring open.

The expansion apparatus of this invention is illustrated in FIGS. 3, 4, 5, 6 wherein a tubular closed end cell 20 is secured to the forward end of a tube 21 extending from a hypodermic syringe 22 or other controllable source of pressurized fluid, preferably gas, although liquids might be used. The preferred gas is air. The cell 20 preferably has the configuration of a small test tube with a closed end 23 and an open end 24. The cell 20 has an outer diameter preferably from 0.7 to 1.2 millimeters. The cell 20 is preferably made from rubber latex or elastomeric plastic substances such as polyvinylidine chloride. The hypodermic syringe 22 has a plunger 25 which has one or more sealing rings 26 tightly fitted into a syringe bore 27. Calibrations 28 on the syringe 22 permit the operator to determine the location of the sealing ring 26. The operator depresses the plunger 25 as shown in FIG. 4 causing controlled, radial outward expansion of the cell 20 to a balloon configuration 20a as shown in FIG. 4. The diameter of the balloon can be controlled by the position of the plunger 25 within the syringe bore 27. The instantaneous position can be observed by means of the location of the sealing ring 26 with respect to the calibrations 28. After the operator has determined the precise diameter required for the balloon configuration 20a, the plunger 25 is withdrawn and the expandable cell 20 is thus calibrated.

The cell 20 thereafter is introduced into the open end of a blood vessel 10 as shown in FIG. 5. When the operator advances the plunger 25 to the pre-established calibrated location, as shown in FIG. 6, the expandable cell 20 will reproduce a balloon configuration 20a of the desired diameter. The open end 11a of the blood vessel 10 will be uniformly, gently, outwardly stretched to a desired peripheral diameter.

After the balloon configuration 20a is positioned at the open end 11a for a brief time, e.g., 10 to 30 seconds, the plunger 25 can be withdrawn, the expandable cell 20 will collapse and may be withdrawn from engagement with the open end 11a. The open end 11a retains it enlarged bell-like configuration for a period of time sufficient to allow the surgeon to connect it with a similarly expanded end of another vessel.

In order to guarantee that the bubble will occur at the desired location on the cell 20, a number of pretreatments may be provided. For example, in FIG. 7, the wall thickness of the cell membrane may be reduced as indicated at 30 which will provide least expansion resistance in the thin region and assure that the desired bubble will occur at that location. The wall thicknesses may be reduced by special forming procedures or by abrasion of the membrane material in the desired location 30.

Alternatively as shown in FIG. 8, the cell 20 may be introduced into a rigid sleeve 31 and be connected to a source 38 of pressurized fluid. When the interior pressure of the cell 20 is increased, expansion cannot occur within the sleeve 31 and can only occur at the forward end of the cell 20. One or more expansions of the cell under these circumstances will establish a weakening of the membrane walls and result in expansion only at the forward end 32 as shown in phantom outline in FIG. 8.

A further means for directing the location of the bubble is shown in FIG. 9 which is an enclosed chamber 33 having an opening 34 to receive a cell 20 and having a perforated cage 35 shaped around the opening 34. The chamber 33 may be evacuated by withdrawing air through an outlet tube 36. The reduced pressure within the chamber 33 will cause the cell 20 to expand to conform to the perforated gauge 35, thereby weakening the walls of the membrane forming the cell 20 at the desired location for bubble formation.

The cell 20 normally has a thickened wall 37 at the closed end (FIGS. 7, 8, 9) which results from the manufacturing process. The thickened wall 37 causes the normal bottom configuration to appear at a distance from the forward end of the cell 20, as illustrated in FIG. 4.

We claim:

1. In the method for anastomosing a blood vessel end comprising expanding the end of a blood vessel having an inner wall and an outer wall to facilitate anastomosis of the said end with another blood vessel, the improvement comprising:

inserting into the open end of said vessel the closed end of a closed, resilient, expansible tubular member; introducing fluid into the said tubular member to cause controlled radial outward expansion against the said inner wall of said vessel; maintaining said tubular member in an expanded conditions for a sufficient period of time to establish a temporary expansion of the said end of said vessel; thereafter withdrawing the said tubular member from the enlarged end of said vessel and thereafter anastomosing the enlarged end of said vessel to another blood vessel.

2. The method of claim 1 wherein said fluid is gas.

3. The method of claim 1 wherein said fluid is air.

4. The method of claim 1 wherein the said tubular member is a plastic tubing having an outer diameter of 0.7 to 2.5 millimeters.

5. The method of claim 1 wherein the said tubular member, in its expanded condition, has a diameter of 1.5 to 3.0 times the initial outer diameter.

* * * * *